United States Patent
Kinlen et al.

[11] Patent Number: 5,271,820
[45] Date of Patent: * Dec. 21, 1993

[54] SOLID STATE PH SENSOR

[75] Inventors: Patrick J. Kinlen, Fenton; Martin L. Rapp, Grover; David E. Hubbard, Ballwin, all of Mo.

[73] Assignee: Monsanto Company, St. Louis, Mo.

[*] Notice: The portion of the term of this patent subsequent to May 5, 2009 has been disclaimed.

[21] Appl. No.: 901,001

[22] Filed: Jun. 19, 1992

[51] Int. Cl.⁵ .............................................. G01N 27/30
[52] U.S. Cl. ............................. 204/418; 204/433; 204/435
[58] Field of Search ............... 204/433, 435, 415, 416, 204/418, 153.21

[56] References Cited

U.S. PATENT DOCUMENTS

| | | | |
|---|---|---|---|
| 3,726,777 | 4/1973 | Macur | 204/195 |
| 4,507,194 | 3/1985 | Shimomura et al. | 204/435 |
| 4,519,973 | 5/1985 | Cahalan et al. | 264/195 |
| 4,536,274 | 8/1985 | Papadakis et al. | 204/433 |
| 4,734,184 | 3/1988 | Burleigh et al. | 204/409 |
| 4,797,192 | 1/1989 | Takiguchi | 204/412 |
| 4,818,361 | 4/1989 | Burgess et al. | 204/406 |
| 4,818,365 | 4/1989 | Kinlen et al. | 204/433 |
| 4,908,117 | 3/1990 | Kinlen et al. | 204/415 |
| 5,110,441 | 5/1992 | Kinlen et al. | 204/418 |

FOREIGN PATENT DOCUMENTS 136060 5/1989 Japan.

Primary Examiner—Donald R. Valentine
Assistant Examiner—Bruce F. Bell
Attorney, Agent, or Firm—Lawrence L. Limpus

[57] ABSTRACT

A solid state pH sensor having an indicator electrode of metal/metal oxide and a reference electrode of metal/metal salt applied to inert, electrical conductors imbedded in an electrically non-conductive substrate, such as a ceramic substrate. The sensing portion of the sensor preferably has a coating of an annealed perfluorocarbon copolymer. Alternatively, the indicator or reference electrodes may be formed on separate electrically non-conductive substrates with each having an inert electrical conductor imbedded therein. These indicator or reference electrodes may be utilized with each other or with prior art electrodes.

15 Claims, 1 Drawing Sheet

SOLID STATE PH SENSOR

FIELD OF THE INVENTION

This invention relates to a solid state pH sensor having an indicator electrode of metal/metal oxide and a reference electrode of metal/metal salt applied to inert electrical conductors, such as electrically conductive platinum or iridium metal pins, imbedded in an electrically non-conductive substrate, such as electrically non-conductive ceramic substrates including glass substrates.

BACKGROUND OF THE INVENTION

Junction-type metal/metal oxide solid state pH electrodes have been proposed for sensing the pH of solutions and other fluids. These electrodes have the sought after advantages of stability in aqueous solutions over a wide range of temperatures and pressures, low impedance and fast response to pH changes. Fog et al., "Electronic Semiconducting Oxides as pH Sensors", Sensors and Actuators, 5 (1984) 137-146, discuss the limitations of such pH sensors. Oxidizing and reducing agents, such as ferricyanide, ferrocyanide and hydrogen peroxide were found to interfere with pH measurement. Various improvements have been made on the junction-type electrode to make it more rugged and compact.

U.S. Pat. No. 5,110,441 discloses a solid state pH sensor which has an indicator electrode and a reference electrode applied to electrical conductors which are imbedded in an electrically non-conductive substrate. The electrical conductors may be a "cermet material" consisting of ceramic and metallic phases intimately dispersed within one another or metal pins. However, the use of reactive materials, such as the use of brazing compounds, when the conductors are imbedded in the non-conductive substrate, the use of non-inert metallic phases in the cermet material, or the use of reactive metal pins, such as steel pins, can allow corrosive attack caused by the process liquid and by contact between dissimilar materials. Such attack will cause the signal from the pH electrode to drift from the proper measurement and provide incorrect indication of the measured pH.

Thus there exists a need to make a pH electrode which is rugged, compact and free from corrosive attack.

SUMMARY OF THE INVENTION

Accordingly, a feature of the present invention is to provide a pH sensor and electrodes therefore which are applied to inert electrical connectors which are imbedded in and directly bonded to the non-conductive substrate to provide electrodes which are rugged, compact and free from corrosive attack.

More particularly, there is provided a solid state pH sensor for pH sensing equipment, the pH sensor comprising:

(a) an indicator electrode, the indicator electrode comprising
 (1) a first inert electrical conductor imbedded in a first electrically non-conductive substrate, the first inert electrical conductor having a first exposed portion,
 (2) a metal/metal oxide coating on the first exposed portion, such that the metal/metal oxide coating entirely covers the first exposed portion, and
 (3) an indicator contact zone electrically connected to the first inert electrical conductor, wherein the indicator contact zone is utilized in making electrical contact between the first inert electrical conductor and the pH sensing equipment, and (b) a reference electrode, the reference electrode comprising
 (1) a second inert electrical conductor imbedded in a second electrically non-conductive substrate, the second inert electrical conductor having a second exposed portion,
 (2) a metal/metal salt coating on the second exposed portion, such that the metal/metal salt coating entirely covers the second exposed portion, and
 (3) a reference contact zone electrically connected to the second electrical conductor, wherein the reference contact zone is utilized in making electrical contact between the second inert electrical conductor and the pH sensing equipment, (c) wherein the indicator and reference electrodes are electrically insulated from each other and (d) wherein the reference electrode is in contact with a reference electrolyte source.

The inert electrical conductors may be of any suitable inert, conductive material such as, for example, platinum, iridium or gold. However, the inert conductors must be imbedded in the non-conductive substrate without the use of bonding compounds, or other reactive materials, such as by direct bonding between the inert conductor and the non-conductive substrate.

The electrically non-conductive substrate may be of any suitable electrically non-conductive material, for example, electrically non-conductive ceramics, silicon, and synthetic polymers.

Preferably, the foregoing pH sensor further comprises an immobilized electrolyte coating on the metal/metal salt coating as the reference electrolyte source, such that the immobilized electrolyte coating entirely covers the metal/metal salt coating.

More preferably and in addition to the foregoing, the pH sensor further comprises a first perfluorocarbon copolymer coating on the metal/metal oxide coating, such that the first perfluorocarbon copolymer coating entirely covers the metal/metal oxide coating, and a second perfluorocarbon copolymer coating on the immobilized electrolyte coating, such that the second perfluorocarbon copolymer coating entirely covers the immobilized electrolyte coating. It is preferred that the perfluorocarbon copolymer of the first and second perfluorocarbon copolymer coatings is annealed.

The perfuorocarbon copolymer utilized herein is preferably an acid or salt derivation of a base copolymer comprising at least two monomers wherein one monomer is selected from a group consisting of a vinyl fluoride, hexafluoropropylene, chlorotrifluoroethylene, perfluoro-(alkyl vinyl ether) and tetrafluoroethylene, and the second monomer is selected from the group of monomers containing an —$SO_2F$ or —COF group. The base copolymer is then converted to an acid derivative thereof or a salt of this acid derivative. For example, the base copolymer may be converted to the acid or salt derivative thereof by hydrolyzing the base copolymer.

The indicator and reference electrodes of the present invention may be utilized with each other or individually in conjunction with its conventional or prior art reference or indicator electrode counterpart, respectively.

In another embodiment, the indicator and reference electrodes may have a common, single electrically non-conductive substrate wherein a first portion of the single electrically non-conductive substrate takes the place of the first electrically non-conductive substrate and a second portion of the single electrically non-conductive substrate takes the place of the second electrically non-conductive substrate. In such an embodiment, the first and second annealed perfluorocarbon copolymer coatings may be combined into a single annealed perfluorocarbon copolymer coating.

Accordingly, these and other features and advantages of the present invention will become apparent from the following detailed description, wherein reference is made to the figures in the accompanying drawings.

IN THE DRAWINGS

FIG. 1 a side elevation sectional view of a solid state pH sensor embodying the concepts of the present invention, wherein the indicator and reference electrodes thereof utilize a common ceramic substrate.

DESCRIPTION

Figure 1:
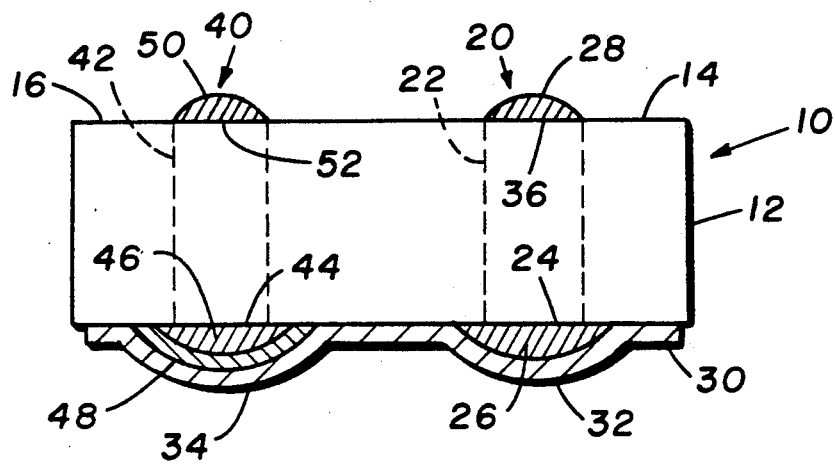

Referring now to the drawings in which like numerals denote similar elements, and more particularly to FIG. 1, there is shown by way of illustration, but not of limitation, a solid state pH sensor (10) for pH sensing equipment (not shown). The pH sensor (10) comprises a ceramic substrate (12) as an electrically non-conductive substrate, an indicator electrode (20) and a reference electrode (40). The indicator electrode (20) and the reference electrode (40) are electrically insulated from each other, in part via the ceramic substrate (12).

The ceramic substrate (12) has a first inert electrical conductor (22) and a second inert electrical conductor (42) imbedded therein without the use of brazing or other bonding compounds, or the use of other reactive materials, such as, for example, by direct bonding between the inert conductor and the non-conductive substrate. "Inert" means materials which will not react in the presence of corrosive liquids nor will they react with dissimilar adjacent materials. It is preferred that the conductors (22) and (42) be formed of platinum, an inert electrically conductive material, which can be imbedded within the ceramic substrate by direct bonding to provide a seal without using brazing compounds or other reactive materials. The first conductor (22) has a first exposed portion (24). Similarly, the second conductor (42) has a second exposed portion (44). Preferably, these two exposed portions (24) and (44) are on the same surface of the ceramic substrate (12).

The ceramic substrate (12) may comprise any one or mixture of ceramic materials. By "ceramic material" it is intended a highly stable material which is substantially electrically non-conductive and has a crystalline structure consisting of metal and non-metal elements. The non-metal element is commonly and preferably oxygen although it may also be carbon or nitrogen. Some of the common metals used as the metal element thereof are aluminum, silicon, magnesium, beryllium, zirconium, titanium, boron and combinations thereof. Examples of suitable ceramic materials would include, but are not limited to, oxides, borides, nitrides, carbides and silicides of the above-mentioned metals; and mixture thereof. The above-mentioned oxides are preferred, with alumina (oxide of aluminum; $Al_2O_3$) and S-glass particularly preferred.

The inert electrical conductors (22) and (42) may comprise any suitable inert, electrically conductive material such as, for example, metal pins formed of platinum, iridium or gold. The conductor material preferably has a thermal expansion coefficient sufficiently similar to that of the ceramic substrate material, so that the conductors (22) and (42) will not separate from or crack the ceramic substrate (12) when subjected to temperature changes.

The indicator electrode (20) comprises a metal/metal oxide coating (26) in electrically conductive contact with the first conductor (22). As depicted in FIG. 1, the metal/metal oxide coating (26) is preferably on the first exposed portion (24), such that the metal/metal oxide coating (26) entirely covers the exposed portion (24). The metal/metal oxide combination utilized in the coating (26) is one suitable for use in junction-type indicator electrodes. Suitable metals for metal/metal oxide combinations would include, but are not limited to, palladium, rhodium, ruthenium, osmium, iridium, platinum, tin, antimony, bismuth, alloys thereof, and mixtures thereof. Suitable metal oxide for the metal/metal oxide combinations would include, but are not limited to, the metal oxides corresponding to the above indicated metals. The metal for the metal portion of this combination may be the same or different from the metal, preferably the same metal, of the metal oxide in the combination. In a preferred embodiment, the metal/metal oxide coating (26) utilizes the combination of iridium/iridium oxide. In an alternate embodiment, the $IrO_2$ may be RF sputtered directly onto the surface of the conductor which has preferably been smoothened by, for example, diamond paste polishing and the metal, e.g. iridium, eliminated.

The metal/metal oxide coating (26) is preferably coated with a first portion (32) of a perfluorocarbon copolymer coating (30), such that the first portion (32) entirely covers the metal/metal oxide coating (26). The first portion (32) acts as a barrier to the migration of anions, but not as to cations, from the environment of interest to the indicator electrode (20). The migration of anions to the indicator electrode (20) can cause interferences in the pH measurement of the environment being studied.

The reference electrode (40) comprises a metal/metal salt coating (46) in electrically conductive contact with the second conductor (42). As depicted in FIG. 1, the metal/metal salt coating (46) is preferably on the second exposed portion (44), such that the metal/metal salt coating (46) entirely covers the exposed portion (44). The metal/metal salt combination utilized in the coating (46) are those suitable for use in junction-type reference electrodes. The metal/metal salt coating (46) comprises an electrically conductive layer of a metal in electrically conductive contact with a layer of a salt of the metal. The metal is preferably selected from one which readily forms an insoluble or poorly soluble salt, preferably an insoluble salt, and has good electrical properties. Examples of such conductive metals are silver, mercury and amalgams with silver being particularly useful and preferred.

The metal/metal salt coating (46) may further comprise a precoating of an electrically conductive substrate. Such a precoating is preferably utilized when improved adhesion to the surface of the ceramic substrate (12) and the second exposed portion (44) is desired. Such a precoating would be an adhesion layer of a metal which adheres well to both and is electrically conductive, for example, titanium and chromium, thereby enhancing the adhesion therebetween.

Often, the ceramic surface causes certain metals, e.g., silver, to form dendrites, i.e., pores and cavities are found in large numbers, when electroplated thereon. As a result, these certain metals do not adhere well to ceramic surfaces. When using these metals, dendrite formation may be avoided by first sputtering the metal onto the surface to be electroplated and then electroplating the metal thereon. The thin layer of sputtered metal provides a better nucleating surface for electroplating metal thereon. Alternatively, dendrite formation may be avoided by using thick film techniques such as using a metal paint or paste which is subsequently buffed.

The metal/metal salt combination utilized in coating (46) is preferably a metal/metal halide or a metal/metal sulfide, more preferably a metal/metal halide and yet more preferably a silver/silver halide. While bromides, chlorides and iodides may be employed as the halide of the metal halide, the metal/metal chloride is preferred, with the silver/silver chloride combination being particularly preferred.

The metal/metal salt coating (46) is placed in contact with a reference electrolyte source containing a known amount of the anion of the metal salt, thereby providing a constant potential. The reference electrolyte source may be, for example, an aqueous solution of known anion concentration, a dried electrolyte layer, or an immobilized electrolyte.

As depicted in FIG. 1, the metal/metal salt coating (46) is preferably coated with an immobilized electrolyte coating (48), such that the immobilized electrolyte coating (48) entirely covers the metal/metal salt coating (46). A second portion (34) of the annealed perfluorocarbon copolymer coating (30) is preferably coated onto the immobilized electrolyte coating (48), such that the second portion (34) entirely covers the immobilized electrolyte coating (48). The second portion (34) eliminates, or at least minimizes, the migration of the electrolytes (anions) in the immobilized electrolyte coating (48) away from the metal salt portion of the metal/metal salt coating (46), thereby assisting in the maintenance of a constant potential for the reference electrode (40).

The immobilized electrolyte coating (48) comprises a polymer which is at least partially cationic, such as quaternary ammonium polymers. Suitable polymers for conversion into cationic polymers include halogenated polymers and amine polymers. What is meant by a halogenated polymer is any halogenated polymer wherein the halogen is susceptible to nucleophilic displacement by a tertiary amine, such as polyvinyl benzyl chloride or polyphosphonitrillic chloride. Such halogenated polymers can be quaternized by any known method of quaternization with a tertiary amine, such as exposing to tertiary amine vapors or soaking in a tertiary amine solution. The quaternized polymer can then be coated on the metal/metal salt coating (46). Alternatively, the halogenated polymer can be coated on the metal/metal salt coating (46) and then quaternized in situ by any of the above methods.

Conversely, amine polymers may be used, which can be quaternized using halogenated compounds to form quaternary amines. The amines must be such that they do not complex with the metal of the reference electrode (40). Tertiary amine polymers are suitable, such as p-dimethylamino polystyrene. The amine must be capable of nucleophilic displacement reaction with the halogenated compound.

The quaternized polymer must be of sufficient molecular weight to form a film or coating on the metal/metal salt coating (46), typically in the range of about 5,000 to about 150,000 daltons. The polymer also is selected to form a film on the metal/metal salt coating (46) such that the perfluorocarbon copolymer coating (30) will adhere to the immobilized electrolyte coating (48). Additionally, the polymer is selected to maximize the concentration of electrolyte in contact with the metal salt of the reference electrode (40) to generate a measurable, stable potential. Insufficient electrolyte will result in interferences from contaminates in the polymer or drift in potential. The preferred halogenated polymer is polyvinylbenzyl chloride, which is a readily available commercial polymer and is easily quaternized.

The perfluorocarbon copolymers utilized in the perfluorocarbon coating (30) are cation exchange polymers which act as a barrier to the migration of anions to the indicator electrode and away from or to the immobilized electrolyte coating (48) of the reference electrode (40) which can cause interferences when measuring pH. Such interferences are characterized by scatter in pH data or no response of the electrode with change in pH. The perfluorocarbon copolymers are preferably annealed so as to improve their permselectivity, i.e., the ability of the polymer to act as a barrier to anions and as a transport for cations.

The annealing procedure involves a heat treating step and a subsequent cooling step. The heat treating step effects a change in the molecular configuration of the copolymer to a molecular configuration which enhances the rejection of hostile or interfering anions by the copolymer. The cooling step is effected such that the molecular configuration attained in the heat treating step is preserved, particularly avoiding contraction and cracking or rapid crystallization of the annealed coating.

Suitable perfluorocarbon copolymers comprise at least two monomers with one monomer being selected from a group including vinyl fluoride, hexafluoropropylene, vinylidene fluoride, trifluoroethylene, chlorotrifluoroethylene, perfluoro (alkylvinyl ether), tetrafluoroethylene and mixtures thereof.

The second monomer contains an $-SO_2F$ or $-COF$ group. Examples of such second monomers can be represented by the formula $CF_2=CFR_1SO_2F$ or $CF_2=CFR_1COF$. $R_1$ in the generic formula is a bifunctional perfluorinated radical having from 1 to 25 carbon atoms. A preferred monomer has from 1 to 8 carbon atoms. One restraint upon the generic formula is a requirement for the presence of at least one fluorine atom on the carbon atom adjacent the $-SO_2F$ or $-COF$ group. The $R_1$ generic formula portion can be of any suitable or conventional configuration, but it has been found preferably that the vinyl radical comonomer join the $R_1$ group through an ether linkage.

The base copolymers are then converted to the perfluorocarbon copolymer utilized herein containing $-SO_3M$ or $-CO_2M$ groups via, for example, hydrolysis, wherein M is hydrogen, an alkali metal, an amine, an ammonium ion or salt, or an alkaline earth metal. The converted copolymer contains sulfonate or carboxylate group based ion exchange sites contained in side chains of the copolymer and attached to carbon atoms having at least one attached fluorine atom. Not all sulfonyl or carbonyl groups within the base copolymer need be converted. The conversion may be accomplished in any suitable or customary manner.

Suitable perfluorocarbon copolymers are commercially available from E.I. du Pont de Nemours and Co., Wilmington, Del. under the trademark Nafion ®.

The indicator electrode (20) and the reference electrode (40) each further comprises an area or zone whereby electrical contact may be made between the respective electrode, (20) and (40), and the pH sensing equipment or instrumentation. Electrical leads may be placed in electrical contact with these contact zones by any suitable manner, for example, by affixing an electrical lead to another exposed portion of the imbedded conductors (22) and (42) or by implanting an electrical lead in the ceramic substrate (12) in electrically conductive contact with the respective imbedded conductors (22) and (42).

As depicted in FIG. 1, the indicator electrode (20) has a contact zone (28) which is electrically connected to the first conductor (22). An electrical lead (86), shown in FIG. 2, may be suitably affixed to the contact zone (28).

In like manner, the reference electrode (40) has a contact zone (50) which is electrically connected to the second conductor (42). An electrical lead (88), shown in FIG. 2, may be suitably affixed to contact zone (50).

The combination of the indicator electrode (20) and the reference electrode (40) form a pH sensor (10). The sensing portion of the pH sensor (10) is preferably coated with an ion-selective membrane, preferably a perfluorocarbon copolymer coating (30) which is preferably annealed. The pH sensor (10) has an indicator and reference contact zone, (28) and (50) respectively, for electrical contact. The electrode (20) and (40) together define an electrical potential between them when the electrodes (20) and (40) are in contact with a solution or electrolyte. By measuring the electrical potential difference between the indicator electrode (20) and the reference electrode (40) at the contract zones (28) and (50), as the pH sensor (10) is immersed in electrolyte, the pH of electrolyte can be determined from this voltage difference.

Figure 2:
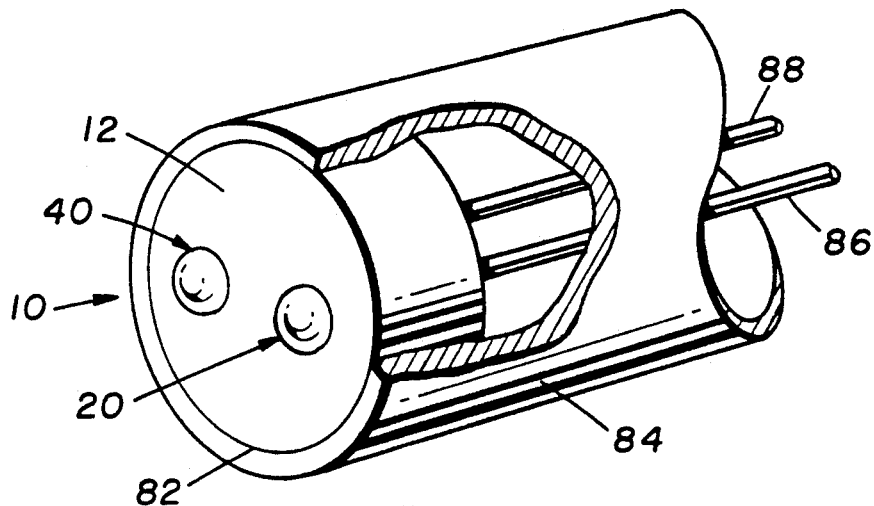
FIG. 2 is a perspective, partially sectional view of the solid state pH sensor of FIG. 1 attached to a housing.

Typically, the contact zones (28) and (50) are electrically insulated and water-proofed. In a preferred embodiment as depicted in FIG. 2. the pH sensor (10) has been attached to a housing (84). The attachment is preferably performed in a seal-less manner, for example, via laser welding or metallizing and brazing the ceramic substrate (12) to the housing (84) producing a weld joint (82). The housing (84) may be of any suitable material, for example, ceramic or metallic. The electrical leads (86) and (88) are placed in electrical contact with the contact zones (28) and (50) prior to attaching the pH sensor (10) to the housing (84). The leads (86) and (88) are attached to the pH sensing equipment (not shown), thereby making electrical contact between the first and second conductors, (22) and (42) respectively, and the pH sensing equipment (not shown).

The housing (84) together with the ceramic substrate (12) and the impervious conductors (22) and (42) serve to chemically and electrically insulate the contact zones (28) and (50) and the leads (86) and (88) from the environment into which the sensor (10) is placed. As such, secondary electrochemical reactions between the environment and these insulated areas are avoided, thereby maintaining the integrity of the pH determination.

The pH sensing equipment may be any suitable or conventional electrical device for measuring electrical output, or for comparing electrical output of an indicator electrode to a reference electrode.

Figure 3:
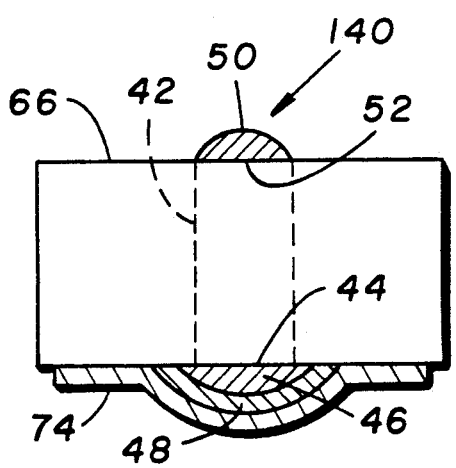
FIG. 3 and FIG. 4 are a side elevation sectional view of a solid state pH sensor embodying the concepts of the present invention, wherein the indicator and reference electrodes thereof utilize separate ceramic substrates.
Figure 4:
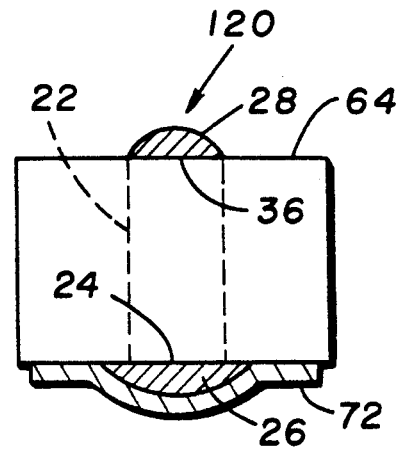

In FIG. 3 and FIG. 4, there is depicted an alternative embodiment of the present invention wherein a first ceramic substrate (64) and a second ceramic substrate (66) are substituted for the first ceramic portion (14) and the second ceramic portion (16) of the ceramic substrate (12) in FIG. 1. Additionally, a first perfluorocarbon copolymer coating (72) and a second perfluorocarbon copolymer coating (74) are substituted for the first perfluorocarbon copolymer portion (32) and the second perfluorocarbon copolymer portion (34) of the perfluorocarbon copolymer coating (30) in FIG. 1, respectively. As a result, a separate indicator electrode (120) and a separate reference electrode (140) are formed corresponding to the indicator electrode (20) and the reference electrode (40) of the pH sensor (10) of FIG. 1. Like the pH sensor (10) in FIG. 2, the separate indicator and reference electrodes (120) and (140), respectively, may be individually attached to their own housing (not shown) with their corresponding electrical leads (not shown).

The separate indicator and reference electrodes (120) and (140), respectively, may be utilized together to form a pH sensor in accordance with the present invention or utilized individually in conjunction with the respective electrode's counterpart, such as those existing within the prior art of indicator and reference electrodes.

PREPARATION OF THE CERAMIC COMPONENT

The ceramic substrate with the conductor(s) imbedded therein for the pH sensor or the separate indicator or reference electrode of the present invention may be manufactured in various ways. An inert, electrical conductor(s) may be encapsulated within a solid ceramic substrate by forming the ceramic substrate on the exterior surface of the conductor(s) by vapor deposition, ion plating, sintering, or sputtering. The ceramic substrate may then be modified to expose at least one portion, preferably two portions, of each of the imbedded conductors.

In another technique, the finely divided solid electrolyte material for the ceramic substrate is press-molded to form a ceramic member having a hole therethrough. Each inert, electrical conductor is inserted into the ceramic substrate to form two exposed portions on opposing surfaces of the ceramic substrate.

In another more preferred technique, the finely divided solid electrolyte material for the ceramic substrate is press-molded and sintered to form a ceramic member. A hole is drilled into and preferably through the ceramic member corresponding to each of the conductors to be imbedded therein. Then, the inert, electrical conductors are inserted to obtain a structure such that each conductor imbedded within the ceramic substrate has at least one, and preferably two, exposed portions.

In each of these techniques, the inert, electrical conductor must be bonded to the substrate by direct bonding without the use of reactive compounds such as typical brazing compounds.

The resulting ceramic substrates are ground to desired thickness and uniform surface finish and then cleaned.

PREPARATION OF THE INDICATOR ELECTRODE

The process for preparing the indicator electrode involves coating the exposed portion of the first inert conductor with a metal/metal oxide coating or a metal oxide coating which is electrically conductive which in turn is coated with the first portion of the annealed perfluorocarbon copolymer coating. The metal/metal oxide coating or the metal oxide coating may be applied by any appropriate means, such as employing one of the thin-film or thick-film techniques. Of these techniques, thin-film techniques are preferred, such as electrode deposition, brazing and sputtering, more preferably sputtering. For the metal oxide portion of the coating, a most preferred method is reactive sputtering, for example, DC Magnetron reactive sputtering or RF reactive sputtering. Reactive sputtering of metal oxides is most preferred because coating thickness, morphology, and stoichiometry may be more effectively controlled utilizing this procedure.

The perfluorocarbon copolymer coating is applied as a solution so as to completely cover the metal/metal oxide coating or the metal oxide coating. The copolymer coating is then dried. The coating and drying steps may be repeated as required to produce a coating which acts as a barrier against the migration of anions to the metal/metal oxide coating or the metal oxide coating. The copolymer coating may be applied by methods, such as spraying, vacuum deposition, dipping or spin-coating. Finally, the copolymer coating is hydrated.

The annealed copolymer possesses better permselectivity than the unchanged copolymer and also possesses enhanced adhesion and lower solubility. Any of the various methods for effecting a change in the morphology of such copolymers may be used.

In a preferred embodiment, the first inert conductor (22) is coated by spin-coating a solution of about 5% to about 15% by weight of Nafion ® 117 perfluorocarbon copolymer of about 1100 equivalent weight in a low aliphatic (up to $C_5$) alcohol and water. The copolymer coating is then dried by any appropriate means to remove the solvent, such as by heating or air drying at room temperature. The coating procedure is repeated, if necessary, until the metal/metal oxide coating or metal oxide coating (26) is entirely coated with a thin film of the perfluorocarbon copolymer, i.e., coating portion (32) or coating (72), which is not thick enough to inhibit the responsiveness of the indicator electrode, (20) or (120), yet sufficient to entirely cover the metal/metal oxide coating or metal oxide coating (26).

The perfluorocarbon copolymer coating, (30) or (72), is then annealed by heat treating the coated indicator electrode to an effective temperature and for a time duration for effecting a change in the molecular configuration of the copolymer which enhances the rejection of anionic interferences and then cooling, preferably to room temperature. Annealing provides enhanced permselectivity of the annealed copolymer coating over the non-annealed copolymer coating.

The preferred method of annealing the copolymer coating involves heating the copolymer coated indicator electrode in an oven initially at room temperature and slowly raising the oven temperature to a maximum temperature of about 250° C. for a period of time sufficient to effect the morphological reconfiguration of the copolymer. If the copolymer is subjected to a temperature in excess of about 280° C., degradation of the copolymer typically occurs. If the copolymer is subjected to a temperature of less than about 150° C., or heated an insufficient amount of time, the morphological reconfiguration has not been observed to occur.

The indicator electrode, (20) or (120), is then cooled by any conventional means that allows slow cooling, preferably down to room temperature.

The coated indicator electrode is hydrated by means such as soaking, heating or boiling in a liquid such as water, water solutions or buffer solutions or exposure to vapors thereof (e.g., steaming). The preferred method is to boil the indicator electrode in a 0.1M solution of phosphate buffer, around pH 7, for about 15 to about 45 minutes. The indicator electrode is then allowed to cool in the solution and is stored in the buffer solution. Once the indicator electrode is hydrated, it is preferably kept hydrated by contacting it with a water source such as storing it immersed in water, buffer solution or other aqueous solutions.

PREPARATION OF THE REFERENCE ELECTRODE

The method for preparing the reference electrode involves coating the exposed portion of the second conductor with a metal/metal salt coating which in turn is preferably coated with an immobilized electrolyte coating. The immobilized electrolyte coating is preferably and at least partially quaternized polymer containing an immobilized electrolyte. The immobilized electrolyte coating is then dried and preferably coated with the second portion of the perfluorocarbon copolymer coating. The perfluorocarbon copolymer coating is dried, and preferably annealed, and subsequently cooled and hydrated.

The metal/metal salt coating may be applied by any appropriate means, such as employing one of the thin-film or thick-film techniques to apply the metal of the metal/metal salt coating to the exposed portion of the second conductor. At least a portion of the metal is then reacted to produce a metal salt, thereby forming the metal/metal salt coating.

In a preferred embodiment, the metal/metal salt coating is a silver/silver chloride coating with the metal being electroplated onto the conductor and substrate. However, direct electroplating of silver onto ceramic surfaces may produce undesirable silver dendrites rather than a smooth, uniform plating. The foregoing may be resolved by precoating the surface with a non-dendrite forming, electrically conductive metal, such as a barrier layer with or without an adhesion layer, prior to coating with silver.

The applied metal of the metal/metal salt coating may be partially converted to the desired metal salt by suitable or conventional chemical or electrochemical techniques.

The metal/metal salt coating of the reference electrode is then placed in contact with a reference electrolyte source containing a known amount of the anion (electrolyte) of the metal salt, thereby providing a constant potential. In a preferred embodiment, the reference electrolyte source is an immobilized electrolyte coating.

The metal/metal salt coating may be coated with the immobilized electrolyte by methods such as spraying, vacuum deposition, dipping or spin coating. For example, a film coating is made on the metal/metal salt coating by spray-coating a solution of about 1 to about 10 percent by weight of an at least partially quaternized, preferably completely quaternized, polymer dissolved or suspended in a solvent such as THF, 2-methoxy ethanol or hexafluoroisopropanol or a mixture of such solvents. Water and methanol may be used as a solvent for the completely quaternized polymer. The partially quaternized halogenated polymer can be prepared by any known method of quaternizing a halogenated polymer. The metal/metal salt coating should be sufficiently coated that upon visual inspection a continuous film or coating is observed on and entirely covering the metal/metal salt coating.

The immobilized electrolyte coating is then dried by evaporation of the solvent at room temperature. The drying process can be accelerated by heating the coated reference electrode to about 100° C. or less.

The immobilized electrolyte coating on the exposed portion of the second conductor is then preferably coated with a perfluorocarbon copolymer to entirely cover the immobilized electrolyte coating. The perfluorocarbon copolymer is applied and dried in the same manner as the perfluorocarbon copolymer coated onto the metal/metal oxide coating of the indicator electrode previously disclosed herein. The perfluorocarbon copolymer coating on the immobilized electrolyte coating is then preferably annealed and cooled in a like manner as with the indicator electrode to effect the desired and previously disclosed morphological reconfiguration of the copolymer to enhance the permselectivity thereof. Herein, the perfluorocarbon copolymer coating acts not only as a barrier against the migration of anions to the immobilized electrolyte coating, but also as a barrier against the migration of anions contained within the immobilized electrolyte coating away therefrom so as to maintain a constant reference potential.

The immobilized electrolyte and perfluorocarbon copolymer coatings of the reference electrode are then hydrated by any appropriate means such as those previously disclosed herein.

The following examples are for illustrative purposes only and are not meant to limit the claimed invention in any manner.

EXAMPLES

Unless otherwise specified, electrode potentials (solid state pH indicator and reference electrodes) were measured versus standard reference electrodes (silver/silver chloride or calomel) using either a Fisher Scientific Model 825 Accumet pH meter or a Model 835 Accumet pH Scanner.

EXAMPLE 1

A platinum pin was imbedded in and direct bonded to an alumina ceramic substrate to form a "feed through" in which the platinum pin was exposed on both sides of the substrate. One exposed surface of the platinum pin was sputter coated with a thin film of iridium metal followed by a thin film of iridium oxide. The electrode was then coated with a solution of Nafion which was annealed, and hydrated. The pH response of the electrode in "Universal Buffer" was as follows (average of several electrodes):
Slope: $-60.9$ mV/pH
Intercept: 662 mV vs. Ag/AgCl
Goodness of Fit:99.90%

EXAMPLE 2

A platinum pin was imbedded in and direct bonded to a glass substrate to form a "feed through" in which the platinum pin was exposed on both sides of the substrate. One exposed surface of the platinum pin was sputter coated with a thin "adhesion" layer of titanium followed by a thin film of iridium metal followed by a thin film of iridium oxide. The electrode was then coated with a solution of Nafion which was annealed and hydrated. The pH response of the electrode in "Universal Buffer" was as follows (average of several electrodes):
Slope $-61.3$ mV/pH
Intercept: 667 mV vs. Ag/AgCl
Goodness of Fit:99.92%

It will be apparent from the foregoing that many other variations and modifications may be made in the apparatus and methods herein before described, by those having experience in this technology, without departing from the concept of the present invention. Accordingly, it should be clearly understood that the apparatus and methods depicted in the accompanying drawings and referred to in the foregoing description are illustrative only and not intended to have limitations on the scope of the invention.

What is claimed is:

1. A solid state pH sensor for pH sensing equipment, said pH sensor comprising:
    an indicator electrode, said indicator electrode comprising a first inert electrical conductor imbedded in a first electrically non-conductive substrate, said first inert electrical conductor having a first exposed portion,
    a metal/metal oxide coating on said first exposed portion, such that said metal/metal oxide coating entirely covers said first exposed portion, and
    a contact zone electrically connected to said first inert electrical conductor, wherein said contact zone is utilized in making electrical contact between said first inert electrical conductor and said pH sensing equipment, and
    a reference electrode, said reference electrode comprising a second inert electrical conductor imbedded in a second electrically non-conductive substrate, said second inert electrical conductor having a second exposed portion, a metal/metal salt coating on said second exposed portion, such that said metal/metal salt coating entirely covers said second exposed portion, and a contact zone electrically connected to said second inert electrical conductor, wherein said contact zone is utilized in making electrical contact between said second inert electrical conductor and said pH sensing equipment;
    wherein said indicator and reference electrodes are electrically insulated from each other; and wherein said reference electrode is in contact with a reference electrolyte source.

2. The solid state pH sensor of claim 1 wherein said first inert electrical conductor and said second inert electrical conductor are inert, electrically conducting metallic pins.

3. The solid state pH sensor of claim 2 wherein said inert, electorally conducting metallic pins are formed from an inert, electrically conducting material selected from the group consisting of platinum, iridium and gold.

4. The solid state sensor of claim 1 including an annealed perfluorocarbon copolymer coating on said metal/metal oxide coating and said immobilized electrolyte coating. such that said annealed perfluorocarbon copolymer coating entirely covers said metal/metal oxide coating and said immobilized electrolyte coating.

5. A solid state pH indicator electrode for use with pH sensing equipment comprising:
   (a) a first inert electrical conductor imbedded in a first electrically non-conductive substrate, said first inert electrical conductor having a first exposed portion,
   (b) a metal/metal oxide coating on said first exposed portion, such that said metal/metal oxide coating entirely covers said first exposed portion, and
   (c) a contact zone electrically connected to said first inert electrical conductor, wherein said contact zone is utilized in making electrical contact between said first inert electrical conductor and said pH sensing equipment.

6. The solid state pH indicator electrode of claim 5 wherein said first inert electrical conductor is imbedded in said first electrically non-conductive substrate without the use of reactive compounds.

7. The solid state pH indicator electrode of claim 5 wherein said first inert electrical conductor is an inert, electrically conducting metallic pin.

8. The solid state pH indicator electrode of claim 7 wherein said inert, electrically conducting metallic pin is formed from an inert, electrically conducting material selected from the group consisting of platinum, iridium and gold.

9. The solid state pH indicator electrode of claim 5 including an annealed perfluorocarbon copolymer coating on said metal/metal oxide coating. such that said first annealed perfluorocarbon copolymer coating entirely covers said metal/metal oxide coating.

10. A solid state pH reference electrode for use with pH sensing equipment comprising:
    (a) a first inert electrical conductor imbedded in a first electrically non-conductive substrate, said first inert electrical conductor having a first exposed portion,
    (b) a metal/metal salt coating on said first exposed portion, such that said metal/metal salt coating entirely covers said first exposed portion,
    (c) an immobilized electrolyte coating on said metal/metal salt coating. such that said immobilized electrolyte coating entirely covers said metal/metal salt coating, and
    (d) a contact zone electrically connected to said first inert electrical conductor. wherein said contact zone is utilized in making electrical contact between said first inert electrical conductor and said pH sensing equipment.

11. The solid state pH indicator electrode of claim 10 wherein said first inert electrical conductor is imbedded in said first electrically non-conductive substrate without the use of reactive compounds.

12. The solid state pH indicator electrode of claim 10 wherein said first inert electrical conductor is an inert, electrically conducting metallic pin.

13. The solid state pH indicator electrode of claim 12 wherein said inert, electrically conducting metallic pin is formed from an inert, electrically conducting material selected from the group consisting of platinum, iridium and gold.

14. The solid state pH indicator electrode of claim 10 including an annealed perfluorocarbon copolymer coating on said immobilized electrolyte coating, such that said annealed perfluorocarbon copolymer coating entirely covers said immobilized electrolyte coating.

15. A solid state pH sensor for pH sensing equipment, said pH sensor comprising:
    an indicator electrode, said indicator electrode comprising a first platinum conductor imbedded in a first portion of an electrically non-conductive substrate without the use of reactive compounds, said first platinum conductor having a first exposed portion,
    a metal/metal oxide coating on said first exposed portion, such that said metal/metal oxide coating entirely covers said first exposed portion, and
    a contact zone electrically connected to said first platinum conductor, wherein said contact zone is utilized in making electrical contact between said first platinum conductor and said pH sensing equipment, and
    a reference electrode, said reference electrode comprising a second platinum conductor imbedded in a second portion of said electrically non-conductive substrate without the use of reactive compounds, said second platinum conductor having a second exposed portion,
    a metal/metal salt coating on said second exposed portion, such that said metal/metal salt coating entirely covers said second exposed portion,
    an immobilized electrolyte coating on said metal/metal salt coating, such that said immobilized electrolyte coating entirely covers said metal/metal salt coating, and
    a contact zone electrically connected to said second platinum conductor, wherein said contact zone is utilized in making electrical contact between said second platinum conductor and said pH sensing equipment;
    wherein said indicator and reference electrodes are electrically insulated from each other.

* * * * *